(12) United States Patent
Reiss

(10) Patent No.: US 6,379,713 B1
(45) Date of Patent: Apr. 30, 2002

(54) METHOD OF TREATING AN ITCH WITH IODINE

(76) Inventor: André Reiss, 147-47 Village Rd., New York, NY (US) 11435

( * ) Notice: Subject to any disclaimer, the term of this patent is extended or adjusted under 35 U.S.C. 154(b) by 0 days.

(21) Appl. No.: 09/816,031

(22) Filed: Mar. 23, 2001

(51) Int. Cl.$^7$ .......................... A61K 33/18; A61K 9/14; A61K 9/70; A61F 13/00

(52) U.S. Cl. .................. 424/667; 424/402; 424/443; 424/445; 424/446; 424/489; 514/817; 514/829; 514/830; 514/831; 514/858; 514/860; 514/861; 514/862; 514/863; 514/864; 514/865; 514/886; 514/887

(58) Field of Search ................... 424/667–672, 424/402, 443, 445, 446, 489; 514/817, 829–831, 862–864, 886, 887, 858, 860, 861, 865

(56) References Cited

U.S. PATENT DOCUMENTS

| | | | |
|---|---|---|---|
| 1,426,633 A | * 8/1922 | Harding | 604/26 |
| 3,777,754 A | * 12/1973 | Plachy | 604/308 |
| 4,355,021 A | * 10/1982 | Mahl et al. | 424/443 |
| 4,416,886 A | 11/1983 | Bernstein | 424/260 |
| 4,564,521 A | 1/1986 | Altadonna | 424/150 |
| 5,591,350 A | * 1/1997 | Piechocki et al. | 210/764 |
| 5,733,270 A | * 3/1998 | Ling et al. | 604/32.6 |
| 5,866,143 A | 2/1999 | Elkhoury | 424/401 |
| 5,869,104 A | 2/1999 | Taylor | 424/680 |
| 6,117,904 A | 9/2000 | Murphy | 514/547 |
| 6,146,640 A | 11/2000 | Dyke | 424/195.1 |
| 6,165,494 A | 11/2000 | Picciano | 424/434 |

OTHER PUBLICATIONS

Derwent Abstract, accession No. 2000–315824, abstracting RU 2130770 (1999).*
Reiss—Wipe Charles with a Disinfectant Sublimate—#09/567,360, Filed May 9, 2000.

* cited by examiner

Primary Examiner—John Pak

(57) ABSTRACT

A method of treatment for a mammal in need of analgesia from an itching skin comprising applying by directional friction against the skin proximate to the itch a composition consisting essentially of dry elemental iodine in the form of an amorphous condensate. The method is found effective in producing analgesia to the affected skin within 1 to 5 minutes after application.

2 Claims, No Drawings

METHOD OF TREATING AN ITCH WITH IODINE

FIELD OF THE INVENTION

The invention relates to a treatment on a mammal in meed of relief from an itching skin comprising topical application of elemental iodine.

BACKGROUND OF THE INVENTION

Analgesic compositions for treating an itch are applied in a dosage of cream, ointment, solution, gel, or lotion, and include:
- a numbing composition such as benzocaine;
- an antihistaminic composition such as diphenhydramine;
- a healing composition such as hydrocortisone; and
- an antibiotic composition such as griseofulvin.

A measure of their effectiveness is the time necessary to stop the immediate itch:
- benzocaine numbs within 5 minutes;
- diphenhydramine and hydrocortisone acetate relieve the urge to scratch after about 15 minutes;
- griseofulvin requires several days to disinfect.

Less common analgesic compositions offered for treating an itch, include:
- U.S. Pat. No. 5,866,143 disclosing morphine cream wiped on skin to relieve itching within 4 minutes.
- U.S. Pat. No. 4,416,886 disclosing naloxone cream wiped on skin to relieve itching within 10 minutes.
- U.S. Pat. No. 6,117,904 disclosing triacetin lotion wiped on skin to promote healing within 24–36 hours.
- U.S. Pat. No. 5,868,104 disclosing a salt block wiped over wet skin to relieve jock itch within several days;

Iodizing skin against infection with a tincture made from crystalline iodine and sodium iodide dissolved in alcohol and water is well known. Topical application of iodine is included in:
- U.S. Pat. No. 6,165,494 offering glycerin and a tincture of iodine to relieve nasal infection in humans within several hours;
- U.S. Pat. No. 6,146,640 offering narrow root and a tincture of iodine to promote healing a skin within days;
- U.S. Pat. No. 4,564,521 offering lemon and a tincture of iodine to relieve a joint pain in humans within a week;
- Ser. No. 09/567,360; filed on May 9, 2000; titled: "Wipe Charged with a Disinfectant Sublimate." offering elemental iodine to disinfect a skin surface.

In summary, an analgesic treatment for relieving a mammal of an itch within 5 minutes seems to require the liquid application of either benzocaine or morphine.

Therefore, an object of the invention is an analgesic treatment for relieving a mammalian skin from an itch.

A second object of the invention is that the treatment is effective within 5 minutes of application.

SUMMARY OF THE INVENTION

A method of treating an itch on a mammalian skin in need of analgesia is disclosed, comprising the steps of:
1. Depositing the amorphous sublimate of crystal iodine onto a fiber applicator in a range of 1 to 30 mg/kg.
2. Rubbing the condensate against the itching skin to supply analgesic in a range of 0.01 to 2 mg/inch$^2$ of skin surface.
3. Waiting for the applied condensate to penetrate under the skin surface and produce analgesia, in a range of 1 to 5 minutes.

The treatment is believed to produce analgesia by iodizing the irritant within the skin. Application of the condensate is found to relieve a mammal from an itch while not wetting or staining the skin.

DESCRIPTION OF THE INVENTION

In a co-pending submittal: Ser. No. 09/567,360; filed on May 9, 2000; titled: "Wipe Charged with a Disinfectant Sublimate", a wipe coated with solid iodine was submitted as useful for treating skin against infection. The Inventor has now unexpectedly found that elemental iodine has analgesic properties. Treatment with the element in the form of an amorphous, tan condensate has been found effective in relieving a mammal from an itch with a single treatment within 1 minute of application.

An itch is believed to be caused by a defensive histamine composition exuded within the skin. Histamine is described as an irritating ammonia derivative that is formed within the skin in response to an allergen. Iodine is believed to produce analgesia by iodizing the histamine into a benign tri-iodide compound. The reaction may be similar to that of adding crystal iodine, ($I_2$), to ammonia water, ($NH_3$), thereby forming an insoluble tri-iodide compound, ($NI_3$).

A concentration of iodine in the range of 0.01 to 2 mg/inch$^2$ of skin surface is found to provide analgesia. An applicator useful for carrying and discharging the analgesic element, in its amorphous form, has been made by loading cotton fiber over a bed of hard iodine crystals sitting at the bottom of a fuming chamber. The bottom of the fiber stack is placed in contact to the top of the iodine bed. By warming the crystals, the reservoir fiber is charged with a fine, soft, rising tan colored sublimate of the hard crystal. At a temperature of 35.deg.C., 2 days is sufficient to charge a fiber with sublimated iodine in a range, by weight, of 1 to 30 mg/g of the wipe fiber. The charged fiber has a tan color, appearing as of having been dipped in liquid iodophor and then dried. Individual crystals of iodine are not readily observed and the charged wipe feels softer than the original fiber. On dipping the charged fiber in water, its tan coloration disappears.

Condensing the fumes from crystalline iodine on a fiber carrier serves to deposit a soft, smoke like, tan colored, amorphous particulate without evidence of injurious iodine crystals. Crystallization of the soft particulate is avoided by limiting the weight of iodine deposited on the fiber. The weight of condensate deposited on a cotton applicator is limited to about 30 mg/g before the condensate deposit begins to precipitate hard, black iodine crystals.

Itching skin is found to be efficiently treated by rubbing the cotton fiber coated with condensed iodine against the itch. Applied in a forceful back and forth motion, the treatment serves to: 1) remove surfaced irritants; 2) develop frictional heat to improve penetration by the condensate; 3) relieve the mammal's urge to scratch within three minutes of its application. The time frame between treatment and analgesia is found comparable to that of benzocaine and morphine.

The skin is not irritated by treatment from a wipe preferably comprising about 10 mg of condensate per gram of fiber comprising cotton. The treatment does not tincture or wet the skin, making the treatment aesthetically pleasing. A preferred treatment supplies about 0.05 to 1 mg/inch$^2$ of skin. An iodine concentration of over 2 mg/inch$^2$ of skin begins to cause pain, while still relieving the itch.

While the invention has been particularly shown and described with reference to preferred embodiments thereof, it will be understood by those skilled in the art that other changes in form and details may be made therein without departing from the spirit and scope of the invention. In particular, it will be obvious to those of skill in the art that this discovery is based on the properties of elemental iodine as applied rather than on the material used as the applicator.

EXAMPLES OF THE INVENTION

The wipe material was obtained from Leasco Co., Brooklyn, N.Y. Crystal iodine was obtained from Baddley Chemicals Corp, Baton Rouge, La. In separate cylindrical fuming chambers, three 64 gram sample lots of 80 wipes each were exposed to 200, 500, and 800 mg of crystal iodine at 35.deg.C. The wipes were charged until the coarse crystals had disappeared and the fiber had obtained a uniform tan color.

The chamber containing 500 mg of iodine was found to fully coat the 80 wipes with a particulate deposit without precipitating any hard iodine crystals. Three of these wipes were used in the Examples. Each wipe was calculated to be coated with about 6 mg of tan condensate.

Example 1

Wipe sample #1, was rubbed on skin behind a knee inflamed by an allergen, whereupon the skin was found to stop itching within 30 seconds of application. The skin was not further irritated and a staining red color did not visibly appear. The affected skin area was noticed to heal normally.

Example 2

Wipe sample #2, was used to treat an itching forearm skin surface, inflamed by a mosquito bite. The wipe was rubbed back and forth on the bite lump four or five times. The itching was noticed to stop within 3 minutes of application. The skin did not appear visibly stained.

Example 3

Wipe sample #3, was used to treat an itching dog by rubbing the wipe over the hairy skin. The dog stopped scratching immediately and began licking the treated surface.

I claim:

1. An analgesic method of treatment for a mammal in need of relief from an itching skin comprising the steps: (i) causing crystalline iodine to sublime onto a fiber applicator and depositing a tan colored amorphous sublimate onto said fiber applicator in a range of 1 to 30 mg of the sublimate per kg of the fiber applicator; and (ii) rubbing the fiber applicator against the itching skin to supply 0.01 to 2 mg of the sublimate per square inch of said skin; wherein effective analgesic relief of the skin from itching is provided within 1 to 5 minutes after the completion of step (ii).

2. The method of claim 1, wherein the sublimate in the fiber applicator is applied by directional friction against the affected skin surface proximate to the skin.

* * * * *